US00PP35535P2

(12) United States Plant Patent
van Sambeek

(10) Patent No.: US PP35,535 P2
(45) Date of Patent: Dec. 12, 2023

(54) ***VERONICA* PLANT NAMED 'DOVERCANHOPI'**

(50) Latin Name: *Veronica hybrida*
Varietal Denomination: Dovercanhopi

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/119,736

(22) Filed: Mar. 9, 2023

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Veronica* plant named 'Dovercanhopi', characterized by its relatively compact and upright plant habit; moderately vigorous growth habit and moderate growth rate; freely basal branching habit; freely flowering habit on first year's growth; dense inflorescences with numerous purplish red-colored flowers; and good perfotmance as a container and garden plant.

2 Drawing Sheets

Figure 1:
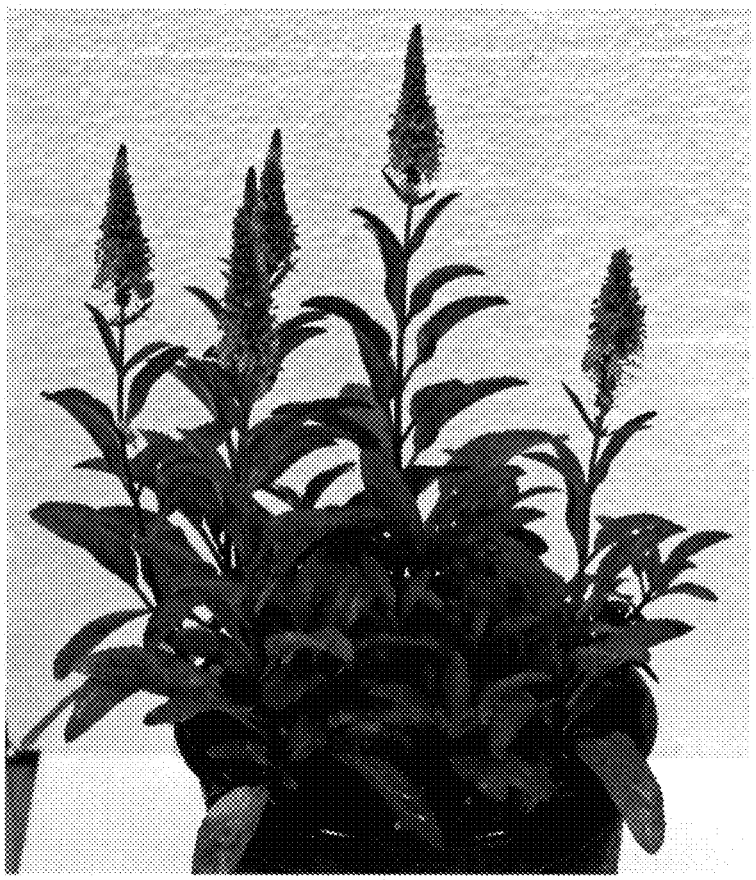

Botanical designation: *Veronica hybrida.*
Cultivar denomination: 'DOVERCANHOPI'.

PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Nov. 4, 2022, application number 2022/2474. Foreign priority is not claimed to this application.

BACKGROUND OF THE INVENTION

The present invention relates to a new and distinct cultivar of *Veronica* plant, botanically known as *Veronica hybrida*, typically grown as a container or garden plant and hereinafter referred to by the name 'Dovercanhopi'.

The new *Veronica* plant is a product of a planned breeding program conducted by the Inventor in Aalsmeer, The Netherlands. The objective of the breeding program is to create new *Veronica* plants with attractive flowers arranged on long inflorescences and good container and garden performance.

The new *Veronica* plant originated from an open-pollination in April, 2016 of an unidentified proprietary selection of *Veronica hybrida*, not patented, as the female, or seed, parent with an unknown proprietary selection of *Veronica hybrida* as the male, or pollen, parent. The new *Veronica* plant was discovered and selected by the Inventor as a single flowering plant from within the progeny of the stated open-pollination in a controlled greenhouse environment in Aalsmeer, The Netherlands in June, 2017.

Asexual reproduction of the new *Veronica* plant by terminal stem cuttings in a controlled greenhouse environment in Aalsmeer, The Netherlands, since June, 2017 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dovercanhopi'. These characteristics in combination distinguish 'Dovercanhopi' as a new and distinct *Veronica* plant:

1. Relatively compact and upright plant habit.
2. Moderately vigorous growth habit and moderate growth rate.
3. Freely basal branching habit.
4. Freely flowering habit on first year's growth.
5. Dense inflorescences with numerous purplish red-colored flowers.
6. Good performance as a container and garden plant.

Plants of the new *Veronica* differ primarily from plants of the female parent selection in time to flower as plants of the new *Veronica* flower earlier than plants of the female parent selection.

Plants of the new *Veronica* can be compared to plants of *Veronica longifolia* 'Vernique Dark Blue', not patented. In side-by-side comparisons, plants of the new *Veronica* differ primarily from plants of 'Vernique Dark Blue' in flower color as plants of the new *Veronica* have purplish red-colored flowers whereas plants of 'Vernique Dark Blue' have dark blue-colored flowers. In addition, plants of the new *Veronica* flower earlier than plants of 'Vernique Dark Blue'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'Dovercanhopi' grown in a container.

Figure 2:
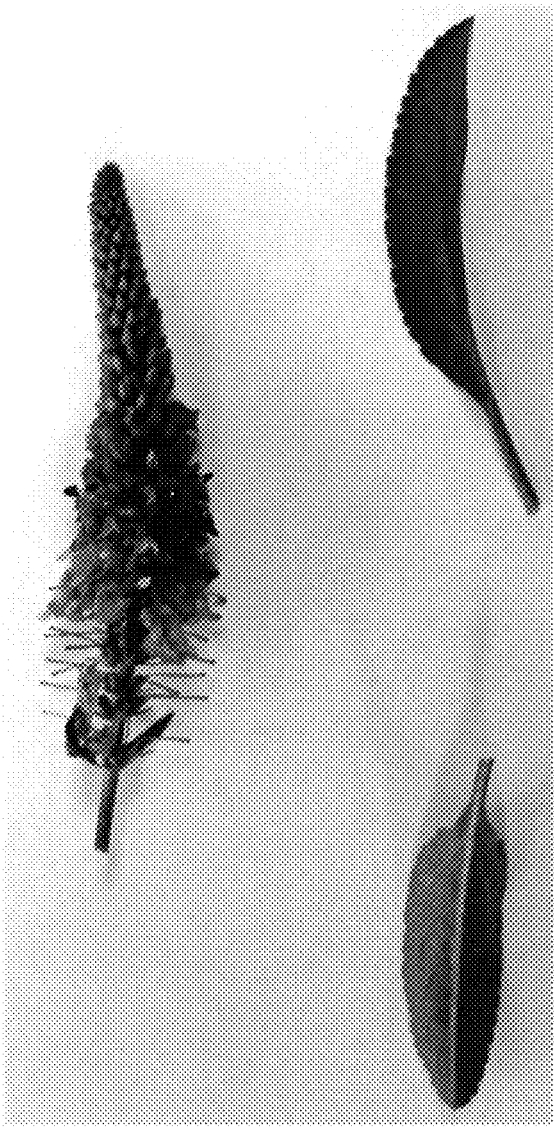

The photograph on the second sheet (FIG. 2) comprises close-up views of a typical inflorescence and the upper and lower surfaces of typical leaves of 'Dovercanhopi'.

DETAILED BOTANICAL DESCRIPTION

Plants used for the aforementioned photographs and following description were grown in 17-cm containers during the summer in a glass-covered greenhouse in Aalsmeer, The Netherlands and under cultural practices typical of commercial *Veronica* production. During the production of the plants, day temperatures averaged 21C and night temperatures averaged 15C. Plants were 19 weeks old when the photographs and the description were taken. In the following description, color references are made to The Royal Horticultural Society Colour Chart, Fifth Edition, except where general terms of ordinary dictionary significance are used.

Botanical classification: *Veronica hybrida* 'Dovercanhopi'.

Parentage:

*Female, or seed, parent.*—Unidentified proprietary selection of *Veronica hybrida*, not patented.

*Male, or pollen, parent.*—Unknown proprietary selection of *Veronica hybrida*, not patented.

Propagation:

*Type cutting.*—Terminal stem cuttings.

*Time to initiate roots, summer.*—About 16 days at temperatures about 26C.

*Time to initiate roots, winter.*—About 21 days at temperatures about 23C.

*Time to produce a rooted young plant, summer.*—About 24 days at temperatures about 23C.

*Time to produce a rooted young plant, winter.*—About 28 days at temperatures about 18C.

*Root description.*—Medium in thickness, fibrous; typically white to light yellow in color, actual color of the roots is dependent on substrate composition, water quality, fertilizer type and formulation, substrate temperature and physiological age of roots.

*Rooting habit.*—Moderately freely branching; medium density.

Plant description:

*Plant type.*—Herbaceous perennial.

*Plant and growth habit.*—Relatively compact and upright plant habit with long and dense inflorescences; overall plant shape, oblong to narrowly oblong; moderately vigorous growth habit and moderate growth rate.

*Plant height, soil level to top of foliar plane.*—About 17 cm.

*Plant height, soil level to top of floral plane.*—About 24 cm.

*Plant width.*—About 23 cm.

*Lateral branch description.*—Branching habit: Freely basal branching habit with about twelve primary stems per plant each with up to two secondary branches; pinching is not required, but will enhance lateral branching potential. Length (excluding inflorescence): About 23 cm. Diameter: About 3 mm. Internode length: About 2 cm. Strength: Strong. Aspect: Erect to about 20 degrees from vertical. Texture and luster: Smooth, glabrous; glossy. Color, developing: Close to 144B. Color, developed: Close to 59A.

Leaf description:

*Arrangement.*—Opposite, single.

*Length.*—About 6 cm.

*Width.*—About 1.7 cm.

*Shape.*—Lanceolate.

*Apex.*—Acute.

*Base.*—Obtuse.

*Margin.*—Crenate with shallow and divergent indentations.

*Texture and luster, upper and lower surfaces.*—Smooth, glabrous; glossy.

*Venation pattern.*—Pinnate and reticulate.

*Color.*—When opening, upper surface: Close to N137D. When opening, lower surface: Close to 137B. Fully expanded leaves, upper surface: Close to 146A; venation, close to 146A. Fully expanded leaves, lower surface: Close to 146C; venation, close to 146C.

*Petioles.*—Length: About 2 cm. Diameter: About 2 mm. Strength: Relatively weak. Texture and luster, upper and lower surfaces: Smooth, glabrous; glossy. Color, upper surface: Close to 143B. Color, lower surface: Close to 144B.

Flower description:

*Flower arrangement and shape.*—Single campanulate flowers arranged on dense terminal racemes; flowers face mostly outwardly.

*Flowering habit.*—Freely flowering habit with about 115 flowers per inflorescence and about 1,860 flowers developing per plant during the flowering season.

*Fragrance.*—None detected.

*Natural flowering season.*—Long flowering period; plants flower continuously from June to August in The Netherlands; plants begin flowering about ten weeks after planting; flowers not persistent.

*Flower buds.*—Length: About 4 mm. Diameter: About 2 mm. Shape: Elliptic. Texture and luster: Smooth, glabrous; matte. Color: Close to 67A.

*Inflorescence height (length).*—About 7 cm.

*Inflorescence diameter.*—About 2 cm.

*Flower diameter.*—About 6 mm by 9 mm.

*Flower length.*—About 6 mm.

*Throat diameter.*—About 1 mm.

*Tube length.*—About 2 mm.

*Tube diameter.*—About 2 mm.

*Petals.*—Quantity and arrangement: Four in a single whorl; petals fused proximally. Length: About 4 mm. Width: About 4 mm. Shape: Rhomboid; concave. Apex: Acute. Margin: Entire; moderately undulate. Texture and luster, upper and lower surfaces: Smooth, glabrous; matte. Texture and luster, throat and tube: Smooth, glabrous; matte. Color: When opening, upper and lower surfaces: Close to 67A. Fully opened, upper and lower surfaces: Close to 67A; venation, close to 67A; color does not change with subsequent development. Throat and tube: Close to 67A; venation, close to 67A.

*Sepals.*—Quantity and arrangement: Four arranged in a single whorl and fused at the base. Length: About 2 mm to 3 mm. Width: About 1 mm. Shape: Subulate. Apex: Acuminate. Base: Fused. Margin: Entire. Texture and luster, upper and lower surfaces: Smooth, glabrous; matte. Color: When opening and fully opened, upper surface: Close to 144A. When opening and fully opened, lower surface: Close to 144A.

*Peduncles.*—Length: About 2 cm. Diameter: About 2 mm. Aspect: Primary peduncles, upright; secondary peduncles, about 10 degrees from main peduncle axis. Strength: Moderately strong. Texture and luster: Smooth, glabrous; glossy. Color: Close to 144B.

*Pedicels.*—Length: About 1 mm. Diameter: Less than 1 mm. Aspect: About 60 to 90 degrees from peduncle axis. Strength: Relatively weak. Texture and luster: Smooth, glabrous; glossy. Color: Close to 144A.

*Flower bracts.*—Length: About 5 mm. Width: About 1 mm. Shape: Acicular. Texture: Smooth, glabrous. Color: Close to 137A.

*Reproductive organs.*—Stamens: Quantity per flower: Two. Filament length: About 7 mm. Filament color: Close to 70B. Anther shape: Roughly oblong. Anther size: About 1 mm by 2 mm. Anther color: Close to 79A. Pollen amount: Moderate. Pollen color: Close to 155A. Pistils: Quantity per flower: One. Pistil length: About 7 mm. Stigma diameter: Less than 1 mm. Stigma shape: Capitate. Stigma color: Close to N79A. Style length: About 6 mm. Style color: Close to 79B. Ovary color: Close to N144A.

*Seeds and fruits.*—To date, seed and fruit development has not been observed on plants of the new *Veronica.*

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −35C to about 30C and to be suitable for USDA Hardiness Zones 4 through 9.

It is claimed:

1. A new and distinct *Veronica* plant named 'Dovercanhopi' as illustrated and described.

* * * * *